United States Patent [19]

Kaplan

[11] Patent Number: 4,726,378
[45] Date of Patent: Feb. 23, 1988

[54] ADJUSTABLE MAGNETIC SUPERCUTANEOUS DEVICE AND TRANSCUTANEOUS COUPLING APPARATUS

[75] Inventor: Morton R. Kaplan, Santa Barbara, Calif.

[73] Assignee: Minnesota Mining and Manufacturing Company, St. Paul, Minn.

[21] Appl. No.: 850,863

[22] Filed: Apr. 11, 1986

[51] Int. Cl.$^4$ ............................................. A61N 1/00
[52] U.S. Cl. ............................................. 128/419 R
[58] Field of Search ............... 128/654, 639, 1.3, 1 R, 128/419 R, 783, DIG. 25; 179/107 BC; 464/29; 604/332, 338, 339

[56] References Cited

U.S. PATENT DOCUMENTS 3,952,726 4/1976 Hennig et al. ............... 128/DIG. 25
4,352,960 10/1982 Dormer et al. .

Primary Examiner—Kyle L. Howell
Assistant Examiner—J. P. Lacyk
Attorney, Agent, or Firm—Donald M. Sell; James A. Smith; William D. Bauer

[57] ABSTRACT

An externally worn body device adapted to be magnetically held supercutaneously with a case being separable into first and second parts and being releasably secured together. The case contains a magnetic device for magnetically holding the case in a supercutaneous position with the magnetic field strength at the surface of the case adjacent to the supercutaneous position being adjustable. The magnetic device may also be adjustable in magnetic polarity. The externally worn body device may contain a transmitting coil positioned within the case for transmitting an electrical signal intended for transcutaneous reception. The externally worn body device may be combined with an implanted subcutaneous member which contains a magnetic device for providing an appropriate magnetic attraction to the corresponding supercutaneous magnetic device. The subcutaneous member may contain a receiving coil designed to cooperate with the transmitting coil of the externally worn body device for the reception of the transcutaneous electrical signals.

20 Claims, 3 Drawing Figures

ADJUSTABLE MAGNETIC SUPERCUTANEOUS DEVICE AND TRANSCUTANEOUS COUPLING APPARATUS

BACKGROUND OF THE INVENTION

This invention relates generally to an apparatus for coupling a member implanted in a body with a member located outside of the body. More particularly the present invention is related to magnetic devices for magnetically holding and aligning the external member supercutaneously with respect to an implanted subcutaneous member.

There exist many devices in which it is desirable to impart an electrical signal to an internal location in a body. One prime example is to facilitate electrical stimulation of the auditory nerve. In these devices, an electrode is implanted in or near the cochlea of a patient and an electrical wire transmits electrical signals to the electrode which may ultimately be interpreted by the patient as representations of sound. Other devices in which it is desirable to impart an electrical signal to an internal location in the body may include heart pacers, neuromuscular stimulators and bone growth stimulators. In each of these devices it may be necessary or desirable to impart a subcutaneous electrical signal.

In order to impart electrical signals across the skin boundary, usually either a percutaneous plug is used to directly connect the wire or else an external device is located supercutaneously proximate an implanted subcutaneous device. Percutaneous plugs generally are not desirable due to the possibility of infection. When an external supercutaneous device and an implanted subcutaneous device are used, information may be transmitted electrically across the skin boundary without requiring a direct through the skin wire connection.

Where an external supercutaneous transmitter is utilized in conjunction with an implanted subcutaneous receiver, it is important to hold the external device close to the skin boundary in order to maintain a known constant physical separation between the external transmitter and the implanted receiver. It is also important to maintain accurate lateral alignment of the transmitter and receiver with respect to each other. Errors in either of these positioning constraints can cause deteriorations in the signal being received by the implanted subcutaneous receiver.

One known mechanism for holding an external device in place is with an ear hook designed to mechanically hold the external device to the external ear. Similarly, eye glass frame structures have been used to mechanically hold an external device in place. However, in both of these cases, misalignment is common due to slippage or mechanical displacement of the mechanical device from its intended position.

Another known mechanism for holding an external device in place is described in U.S. Pat. No. 4,352,960, Dormer et al, Magnetic Transcutaneous Mount for External Device of an Associated Implant. In Dormer, a magnetic device is located in an implanted receiver. Another magnetic device is located in the external transmitter. Magnetic attraction between these two magnetic devices holds the external transmitter closely against the skin and also closely in lateral alignment. Such a system provides advantages in maintaining critical spacing and alignment of an external transmitter with a subcutaneous receiver.

Because of differences in thickness of different individual skin and differences in sensitivities to pressure against the skin, differing magnetic attractive forces for the external devices worn by differing persons are desirable. If an individual's skin thickness is greater than the norm, then the spacing between the magnetic devices is greater. In order to provide the same attractive force between the supercutaneous and subcutaneous magnetic devices, a stronger magnetic device either external or implanted is required. Since the implanted magnetic device cannot be readily changed due to the surgery involved usually in order to change the magnetic force of the supercutaneous magnetic device must be modified. Also, differences in the actual magnetic attractive force are desirable. This is because the attractive magnetic force on one individual may be comfortable but the same magnetic attractive force on another individual may cause skin irritation and soreness. It is desirable to be able to vary the magnetic attractive force in order to maintain a comfort level but still adequately hold the external device in place.

Further, it has been known for the implanted device to be implanted upside down during surgery. This error may be first noticed after the surgical wound has healed and the external device is attempted to be utilized in conjunction with the implanted receiver. The upside down implanted receiver would cause a magnetic repulsion of the external device instead of the desired magnetic attraction. Thus, it is also desirable to be able to reverse the magnetic polarity of the external magnetic device.

SUMMARY OF THE INVENTION

The present invention provides an externally worn body device adapted to be magnetically held supercutaneously to the body. The device includes a case which is separable into a first part and a second part which are releasably secured together. A magnetic device is secured within the case when the first and second parts of the case are secured together for magnetically holding the case in the supercutaneous position. The magnetic device is adjustable in magnetic field strength at the surface of the case which is adjacent to the supercutaneous position. In a preferred embodiment, the magnetic device is also adjustable in magnetic polarity. In a preferred embodiment, the device further includes a transmitting device positioned within the case for transmitting an electrical signal intended for transcutaneous reception. In a preferred embodiment, the magnetic field strength is adjusted by replacing at least one permanent magnetic module with another permanent magnetic module of differing magnetic field strength. In a preferred embodiment, the magnetic field strength at the surface adjacent the supercutaneous position is adjustable by providing nonmagnetic spacers between the magnetic device and the surface of the case being held in the supercutaneous position. In still another preferred embodiment, the device includes a resilient insert positioned within the case designed to hold the magnetic device in its closest position allowed to the surface of the case closest the supercutaneous position.

The present invention also provides a transcutaneous coupling apparatus. A first member is positioned subcutaneously with a first magnetic device positioned within the first member for providing an appropriate magnetic attraction to a corresponding supercutaneous magnetic member. A second member is positioned supercutaneously. The second member has a case separable into a first part and a second part and being releasably secured together. A second magnetic device is secured within the case of the second member when the first and second parts of the case are secured together for magnetically holding the case in a supercutaneous position. The magnetic device is adjustable to alter magnetic field strength at a surface of the case adjacent to a supercutaneous position. In a preferred embodiment, the magnetic device is also adjustable in magnetic polarity. In a preferred embodiment, the second member additionally has a transmitting device positioned within the case for transmitting an electrical signal intended for transcutaneous reception and the first member contains a receiving device positioned within the first member for receiving the electrical signal.

In either case, the magnetic attractive force provided by the external device may be adjusted by either (1) exchanging one magnetic device for another magnetic device with a different magnetic field strength, (2) adding to or subtracting from the total number of magnetic devices held within the case, (3) by adding or deleting spacers to change the physical separation of the magnetic device from the surface of the case held most closeley to the supercutaneous position or (4) by reversing the polarity of the magnetic device(s).

Thus, the present invention provides a device which may be easily adjusted in a clinical setting for changes in skin thickness. The present invention provides a device which can be adjusted for changes in magnetic field strength attraction to achieve the desired comfort level of the user. The present invention provides a device which can be adjusted for changes in the direction of the magnetic force to provide magnetic atraction regardless of the magnetic direction of the implanted magnetic device. The present invention provides a highly adaptable device which eliminates the stocking of a wide variety of separate devices with differing magnetic field strengths.

BRIEF DESCRIPTION OF THE DRAWINGS

The foregoing advantages and operation of the present invention will become more readily apparent from the following description and accompanying drawings in which.

DETAILED DESCRIPTION OF THE PREFERRED EMBODIMENTS

The present invention is an improvement over the magnetic device described in U.S. Pat. No. 4,352,960, Dormer et al, Magnetic Transcutaneous Mount for External Device of an Associated Implant, which is hereby incorporated by reference.

Figure 1:
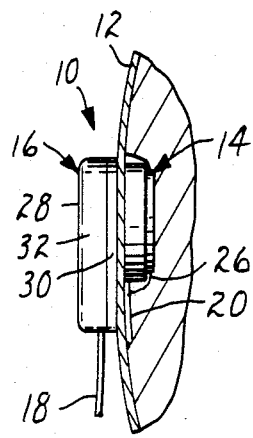
FIG. 1 is side view of a transcutaneous coupling apparatus in place across a cutaneous boundary.

FIG. 1 illustrates the transcutaneous coupling apparatus 10 of the present invention in place across a cutaneous boundary 12 (skin). An internal device 14 is implanted subcutaneously within the body and the cutaneous boundary 12 replaced to completely cover the internal device 14. An externally worn body device 16 is illustrated positioned supercutaneously next to the cutaneous boundary 12. In a preferred embodiment, the externally worn body device 16 contains a transmitting device designed to transmit an electrical signal designed for transcutaneous reception. The transmitting device within externally worn body device 16 receives the electrical signal to be transmitted from an external processor (not shown) via electrical wire 18. In a preferred embodiment, the internal device 14 contains a receiving mechanism for receiving the transcutaneously transmitted electrical signal and sends the received signal along electrical wire 20 to an electrode or other implanted device (not shown) where it can be utilized.

Figure 2:
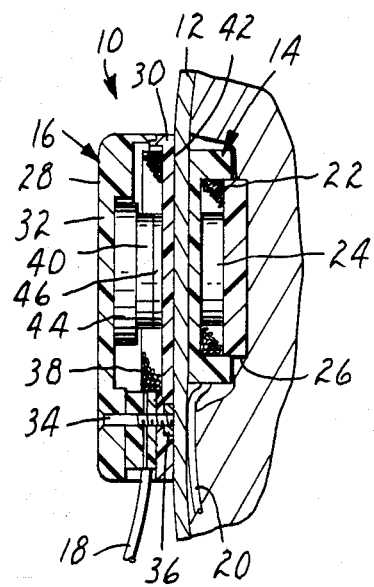
FIG. 2 is cross section of a transcutaneous coupling apparatus in place across a cutaneous boundary.

FIG. 2 illustrates a cross-sectional view of the same transcutaneous coupling apparatus 10 of FIG. 1. The transcutaneous coupling apparatus 10, as in FIG. 1, is shown in place across cutaneous boundary 12. Internal device 14 is shown comprising an electrically conductive coil 22 designed to receive the transmitted electrical signal. Also, positioned within internal device 14 is magnetic device 24. In a preferred embodiment, magnetic device 24 is a permanent magnet and in a still preferred embodiment is a permanent magnet of the rare earth type. Internal device 14 is surgically implanted in the patient under the cutaneous boundary 12 in a fixed position. With respect to cochlear implants usually this is achieved by countersinking the mastoid to receive a lip 26 of the internal device 14.

Externally worn body device 16 consists of a case 28 which is separable into a first part 30 and a second part 32. The first part of the case 30 and the second part of the case 32 are secured together by screw 34 and associated nut 36. Of course, screw 34 and nut 36 may be undone to separate first and second portions, 30 and 32, of case 28 in order to gain access to the inside of case 28. Contained within case 28 is an electrically conductive coil 38 which is coupled to wire 18 which may operate to transmit an electrical signal intended for transcutaneous reception. Holding externally worn body device 16 against the cutaneous boundary and in alignment with internal device 14, and hence spacing and aligning transmitting coil 38 with receiving coil 22, is a magnetic device 40 which, in a preferred embodiment, is positioned within a cavity formed by the hollow core of electrically conductive transmitting coil 38. In a preferred embodiment, magnetic device 40 consists of one or more separate magnetic modules which may be substituted for varying degrees of magnetic field strength and, when more than one are used, may be additive to combine their magnetic field strengths. Magnetic device 40 is held as close as possible to a surface 42 of the case 28 closest the cutaneous position opposite internal device 14 by a resilient insert 44. In a preferred embodiment, the resilient insert 44 consists of a piece of resilient foam which pushes magnetic device 40 toward the surface 42 but which can be compressed to allow for different sizes of magnetic devices 40 or for different numbers of magnetic devices 40. Optionally contained within case 40 are one or more spacers 46. Spacer 46 may be used between magnetic device 40 away from surface 42 in order to space the magnetic device 40 and first surface 42 in order order to slightly decrease the magnetic attraction between the magnetic device 40 and magnetic device 24. With the optional use of one or more spacers 46 of varying thicknesses very precise adjustments in the magnetic field strength of externally worn body device 16 may be made. Also, it is to be recognized that magnetic device 40 may easily be physically reversed within case 28 in order to provide a magnetic force of the opposite direction should it be required to provide an attractive magnetic force to magnetic device 24 which has an opposite polarity with respect to the magnetic device 40.

Figure 3:
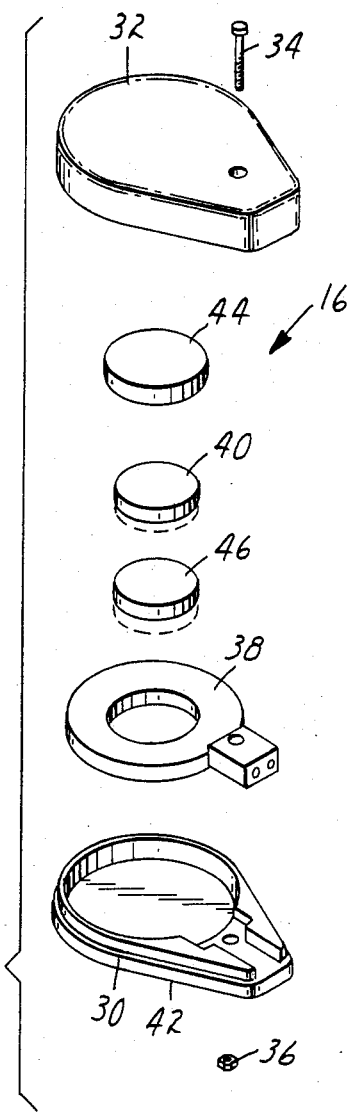
FIG. 3 is an exploded view of the external body device portion of the transcutaneous coupling apparatus.

FIG. 3 illustrates an exploded view of externally worn body device 16. The first part of the case 30, the base of which forms a surface 42 nearest the supercutaneous position, is adapted to receive transmitting coil 38. A cavity formed by the hollow core of transmitting coil 38 forms the space into which magnetic device 40 may be inserted. One or more spacers 46 may be optionally inserted nearest surface 42 to provide precise spacing of the magnetic device 40. One or more magnetic devices 40 which can be of varying degrees of magnetic field strength may also be inserted into the cavity formed by the hollow core of transmitting coil 38. Resilient insert 44 may then be utilized on the side of magnetic device 40 opposite from surface 42 to force magnetic device 40, when externally worn body device 16 is fully assembled, consistently toward surface 42. Resilient insert 44 also allows for adjustments in the physical size of magnetic device 40, differing numbers or sizes of spacers 46 and differing numbers of magnetic devices 40. The second part of case 32 fits over transmitting coil 38, spacers 46, magnetic device 40 and resilient insert 44 to meet with the first part of the case 30. The first part 30 and second part 32 of the case 28 is releasably secured together by means of screw 34 and associated nut 36.

Thus, it can be seen that there has been shown and described a novel, adjustable, magnetic, supercutaneous device and transcutaneous coupling apparatus. It is to be understood that various changes, modifications and substitutions in the form and details of the described device and apparatus can be made by those skilled in the art without departing from the scope of the invention as described by the following claims.

What is claimed is:

1. An externally worn body device adapted to be magnetically held in a supercutaneous position in lateral alignment with a subcutaneous first magnetic element, comprising:
   a case being separable into a first part and a second part;
   securing means operably coupled to said case for releasably securing said first part and said second part of said case together; and
   a second magnetic element contained within said case when said first part and said second part of said case are secured together, said second magnetic element holding said externally worn body device in a supercutaneous position proximate to said subcutaneous first magnetic element, holding said externally worn body device in lateral alignment with said subcutaneous first magnetic element, being axially aligned with said subcutaneous first magnetic element and providing a direct axial magnetic attraction to said subcutaneous first magnetic element; and
   said second magnetic element being adjustable in magnetic field strength at a surface of said case adjacent said supercutaneous position for changing the magnetic field strength attraction between said second magnetic element and said subcutaneous first magnetic element.

2. An externally worn body device as in claim 1 wherein said second magnetic element is also reversible in magnetic polarity.

3. An externally worn body device as in claim 2 which further comprises transmitting means positioned within said case for transmitting an electrical signal intended for transcutaneous reception.

4. An externally worn body device as in claim 1 wherein said second magnetic element comprises at least one permanent magnetic module which may be replaced as an adjustment in magnetic field strength is required.

5. An externally worn body device as in claim 1 wherein said case, when said first part and said second part are secured together, has a cavity for holding said second magnetic element, wherein said second magnetic element comprises at least one permanent magnetic module, and wherein said externally worn body device further comprises at least one spacer positioned within said cavity between said magnetic module and said surface of said case adjacent said supercutaneous position.

6. An externally worn body device as in claim 5 which further comprises a resilient insert positioned within said cavity disposed with respect to said magnetic module opposite from said surface of said case adjacent said supercutaneous position.

7. An externally worn body device as in claim 6 which further comprises transmitting means positioned within said case for transmitting an electrical signal intended for transcutaneous reception.

8. An externally worn body device as in claim 7 wherein said transmitting means comprises an electrically conductive coil having a hollow core.

9. An externally worn body device as in claim 8 wherein said cavity is formed by said hollow core of said electrically conductive core.

10. An externally worn body device as in claim 5 wherein said magnetic module is a rare earth magnet.

11. A transcutaneous coupling apparatus, comprising:
    a first member adapted to be positioned subcutaneously;
    a first magnetic means positioned within said first member for providing an appropriate magnetic attraction to a corresponding supercutaneous magnetic member;
    a second member positioned supercutaneously;
    said second member having a case being separable into a first part and a second part, securing means operably coupled to said case for releasably securing said first part and said second part of said case together;
    a second magnetic element contained within said case when first part and said second part of said case are secured together, said second magnetic element holding said second member in a supercutaneous position proximate to said first member, holding said second member in lateral alignment with said first magnetic means, being axially aligned with said first magnetic means and providing direct axial magnetic attraction to said first magnetic means; and
    said second magnetic element being adjustable and magnetic field strength at a surface of said case adjacent said supercutaneous position for changing the magnetic field strength attraction between said second magnetic element and said first magnetic means.

12. A transcutaneous coupling apparatus as in claim 11 wherein said second magnetic element is also reversible in magnetic polarity.

13. A transcutaneous coupling apparatus as in claim 12 in which said second member further comprises transmitting means positioned within said case for transmitting an electrical signal intended for transcutaneous reception and in which said first member further comprises receiving means positioned within said first member for receiving said electrical signal.

14. A transcutaneous coupling apparatus as in claim 11 wherein said second magnetic means comprises at least one permanent magnetic module which may be replaced as an adjustment in magnetic field strength is required.

15. A transcutaneous coupling apparatus as in claim 12 wherein said case, when said first part and said second part are secured together, has a cavity for holding said second magnetic element, wherein said second magnetic element comprises at least one permanent magnetic module, and wherein said second member further comprises at least one spacer positioned within said cavity between said magnetic module and said surface of said case adjacent said supercutaneous position.

16. A transcutaneous coupling apparatus as in claim 15 wherein said second member further comprises a resilient insert positioned within said cavity disposed with respect to said magnetic module opposite from said surface of said case adjacent said supercutaneous position.

17. A transcutaneous coupling apparatus as in claim 16 in which said second member further comprises transmitting means positioned within said case for transmitting an electrical signal intended for transcutaneous reception and in which said first member further comprises receiving means positioned within said first member for receiving said electrical signal.

18. A transcutaneous coupling apparatus as in claim 17 wherein said transmitting means comprises an electrically conductive coil having a hollow core.

19. A transcutaneous coupling apparatus as in claim 18 wherein said cavity is formed by said hollow core of said electrically conductive core.

20. A transcutaneous coupling apparatus as in claim 15 wherein said magnetic module is a rare earth magnet.

* * * * *